United States Patent [19]

Abe et al.

[11] Patent Number: 5,391,810
[45] Date of Patent: Feb. 21, 1995

[54] METHOD OF CRYSTALLIZING α-L-ASPARTYL-L-PHENYLALANINE METHYL ESTER

[75] Inventors: So Abe; Shinichi Kishimoto; Toshihisa Kato; Hideo Takeda, all of Kawasaki, Japan

[73] Assignee: Ajinomoto Co., Inc., Tokyo, Japan

[21] Appl. No.: 121,569

[22] Filed: Sep. 16, 1993

Related U.S. Application Data

[63] Continuation-in-part of Ser. No. 886,406, May 21, 1992, abandoned.

[30] Foreign Application Priority Data

May 23, 1991 [JP] Japan .................. 3-221336
Apr. 22, 1992 [JP] Japan .................. 4-102917

[51] Int. Cl.⁶ .......................................... C07C 101/02
[52] U.S. Cl. ............................................. 560/41
[58] Field of Search ............... 560/40, 41; 562/445

[56] References Cited

U.S. PATENT DOCUMENTS 4,452,621 9/1982 Fowles ................... 62/534
4,994,605 2/1991 Kishimoto et al. ........ 562/445

Primary Examiner—José G. Dees
Assistant Examiner—Samuel Barts
Attorney, Agent, or Firm—Oblon, Spivak, McClelland, Maier & Neustadt

[57] ABSTRACT

In crystallizing α-APM from a water solution or a mixed solvent solution of water and a lower alcohol in a crystallizer, the pressure in the crystallizer is held at not higher than atmospheric pressure, a water or water/alcohol mixed solution of α-APM is fed into the crystallizer with stirring so that the solvent is vaporized, and the crystallization solution is cooled and crystallized by the latent heat of vaporization or is heated so as to prevent supercooling.

19 Claims, 1 Drawing Sheet

METHOD OF CRYSTALLIZING α-L-ASPARTYL-L-PHENYLALANINE METHYL ESTER

This application is a continuation-in-part of application Ser. No. 07/886,406, filed on May 21, 1992, now abandoned the entire contents of which are hereby incorporated by reference.

BACKGROUND OF THE INVENTION

Field of the Invention

The present invention relates to a method of preparing α-L-aspartyl-L-phenylalanine methyl ester (hereinafter referred to as "α-APM") which is useful as a sweetener and relates to an improved method of α-APM crystallization from a solution of α-APM.

Discussion of the Background

α-APM of the present invention is a dipeptide sweetener having a sweetness about 200 times that of sucrose (cane sugar). Because of its good quality sweetness and the low calorie content, it is widely used as a diet sweetener, and the worldwide demand for it is estimated to be over 10,000 tons by 1995.

α-APM is produced industrially by several methods. One method of obtaining α-APM is to react an N-substituted aspartic acid anhydride and a phenylalanine methyl ester in an organic solvent followed by removal of the N-substituent from the product by a conventional method (U.S. Pat. No. 3,786,039). The thus formed α-APM containing impurities is brought into contact with a hydrohalogenic acid to obtain α-APM hydrohalide, which is neutralized to obtain α-APM. A second method of obtaining α-APM is to methyl-esterify α-L-aspartyl-L-phenylalanine in a mixed solvent comprising water, methanol and hydrochloric acid to obtain α-APM hydrochloride, and then neutralize the hydrochloride to obtain α-APM (Japanese Patent Application Laid-Open No. 53-82752). A third method of obtaining α-APM is to condense an N-substituted aspartic acid and a phenylalanine methyl ester in the presence of an enzyme and thereafter remove the N-substituent from the product (Japanese Patent Application Laid-Open No. 53-135595).

In all of the above-mentioned methods, α-APM is finally crystallized by cooling from an aqueous solution having a relatively high temperature, then the resulting α-APM crystals are separated and dewatered in a solid-liquid separator, such as a centrifugal separator, and thereafter the thus separated crystals are dried. The cooling crystallization is generally carried out in a stirring crystallizer having a heat transfer surface for cooling or in a crystallizer equipped with an external heat exchanger and an external circulation system, such as pumps.

When crystallization of α-APM is carried out by cooling an α-APM-containing solution in a conventional forced flow system crystallizer with a stirring means or external circulation means, the solution always gives fine needle-like α-APM crystals having poor filterability and dewaterability. In addition, in such a system, numerous crystals precipitate and consolidate on the cooling heat transfer surface, whereby the heat transfer efficiency is markedly lowered. Therefore, to remove the consolidated crystal scale the operation of the crystallizer must be frequently stopped.

As a means of overcoming this problem, there is known a method of cooling an aqueous solution of α-APM by conductive heat transfer without effecting any forced flow such as mechanical stirring, to form a pseudo solid phase, optionally followed by further cooling the system (Japanese Patent Application Laid-Open No. 58-177952). In accordance with this method, peeling of the crystals from the cooling surface is extremely easy when discharging the crystal layer (sherbet-like pseudo solid phase), and α-APM crystals having improved filterability and dewaterability in the successive solid-liquid separation step can be obtained. However, where existing or widely-used crystallization equipment is employed, the cooling takes a long time, the efficiency of the method is poor. The discharge causes frequent problems when the method is used with a conventional tank type crystallizer.

A need continues to exist for a means of overcoming the above-mentioned problems in the α-APM crystallization step, i.e., preventing the crystals from forming on the heat transfer surface, decreasing investment in equipment by using an existing or widely-used crystallizer and improving the solid-liquid separability of the crystal slurry.

SUMMARY OF THE INVENTION

Accordingly, one object of the present invention is to provide a process which overcomes the problem of crystal formation on the cooling surface of an α-APM crystallization system (crystallizer).

This and other objects which will become apparent from the following specification have been achieved by the present process. In the present process, when α-APM is crystallized from its aqueous solution the pressure in the crystallizer is kept not higher than atmospheric pressure (760 Torr) so as to concentrate the solution by vaporizing the solvent, whereupon the solution is cooled by the latent heat of vaporization and is thereby crystallized.

BRIEF DESCRIPTION OF THE DRAWING

In FIG. 1, the following designations are used: 1—crystallizer, 2—pressure reducing device, 3—heat exchanger, 4—centrifugal separator, 5—feeding tank, 6—slurry-holding tank, A—APM crystals, B—water/methanol, C—APM wet crystals, and D—mother liquor.

DETAILED DESCRIPTION OF THE PREFERRED EMBODIMENTS

Figure 1:
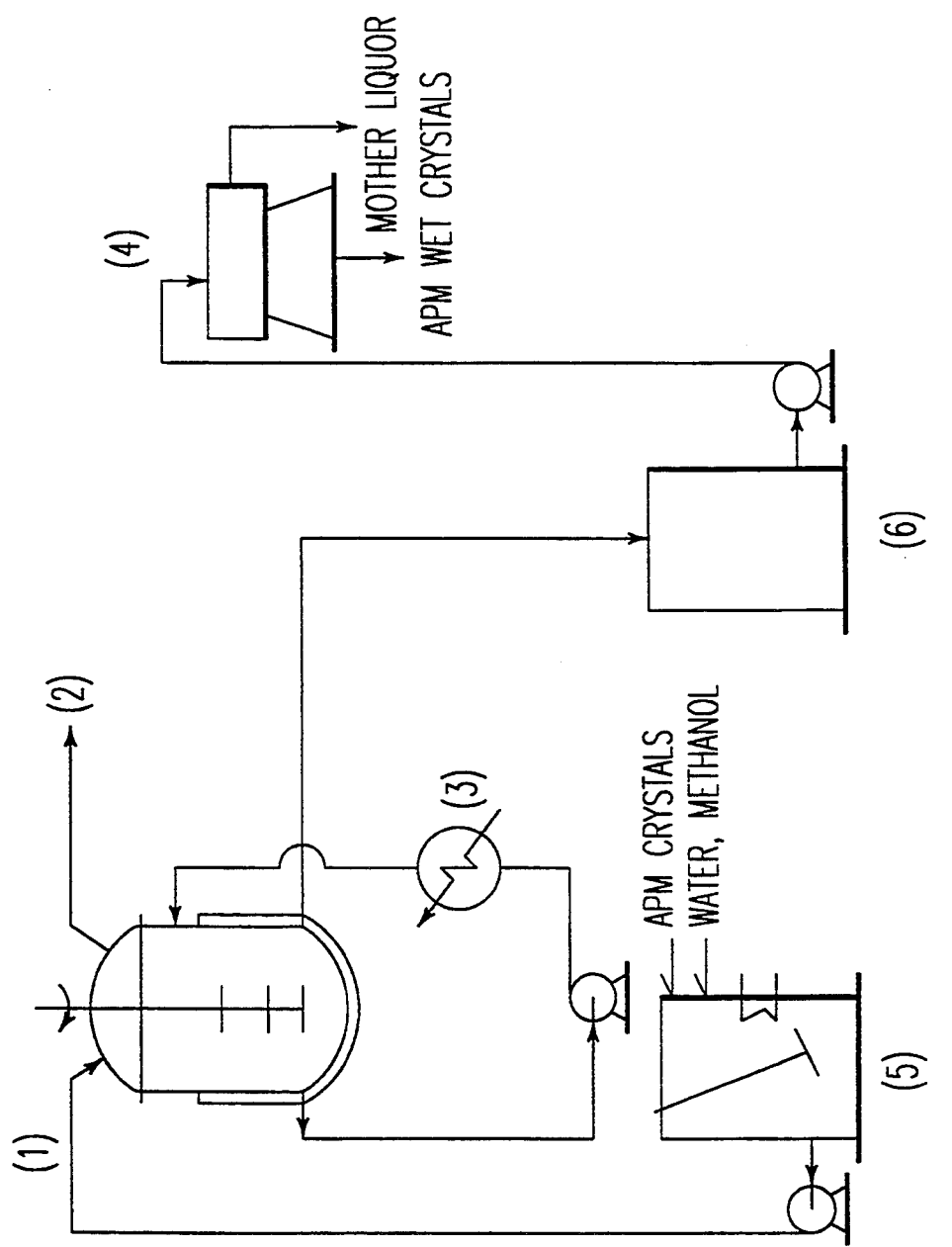
FIG. 1 shows a diagram of crystallizer equipment which can be used in the present invention and was used in Example 1.

A crystallization operation is generally carried out such that, per the unit time, a vaporizing amount of the solvent (water) per vaporizing area of the concentrated solution (or slurry) is about 1,000 kg/m$^2$·hr for the crystallization of ordinary substances other than α-APM. For crystallization of α-APM, however, it has been discovered that a substantial bubbling of the slurry with vaporization occurs under conventional vaporization conditions. This bubbling is especially pronounced when the starting solution is fed to the crystallizer so that the depth of the solution in the crystallizer is kept constant. It is difficult to continue the operation of the equipment under these conditions. It is particularly preferred to control the vaporizing rate to a surprisingly low rate of 40 kg/m$^2$·hr or less, more preferably 20 kg/m$^2$·hr or less, so that long and stable operation is possible.

A higher upper limit for the vaporizing rate is possible when using a mixed solvent of water and a lower alcohol, such as methanol or ethanol, than when using water alone. When using a mixed solvent of water and a lower alcohol, a vaporizing rate of 400 kg/m²·hr or less, more preferably 200 kg/m²·hr is preferred. Further, when using a mixed solvent, equipment productivity is improved as the solubility of α-APM in the mixed solvent above 40° C. is higher than in water alone, and thus the crystals obtained have larger diameters and good solid-liquid separability.

As the apparatus for the present invention, any industrially employable existing or widely-used crystallizer, such as a general stirring crystallizer, a Draft Tube Baffled (DTB) crystallizer, a crystal-Oslo crystallizer or modifications thereof may be used, so long as they have an enclosed structure capable of withstanding the reduced pressure used in the present method. The pressure in the crystallizer is kept at 100 Torr or less, preferably, 50 Torr or less.

Crystallizers are available without heat transfer surfaces for cooling. It is preferable to equip such crystallizers with a heat transfer means such as coils, jackets and so on, or with an external heat exchanger whereby the solution can be heated by circulating a part of the α-APM solution through the heat transfer means. Heating the α-APM solution is preferable when the temperature of the solution becomes too low. When the temperature of the solution becomes too low, the vaporization rate is lowered, thereby decreasing the efficiency of the present process. Although the temperature of operation during the present process depends on the operation pressure, it is preferable to keep the temperature of the solution at 20° C. or lower to obtain maximum stability of the process and high yield of α-APM. The lower limit of the solution temperature is the freezing point of the solvent.

The starting α-APM solution may be fed to the crystallizer continuously, batchwise or a combination of batch and continuous operation. It is preferable to feed the α-APM solution continuously keeping the depth of the solution constant in view of equipment productivity. In this case, yield per equipment volume can be increased by simultaneously discharging the concentrated solution or slurry (continuous vaporization operation).

Since the bubbling is remarkable as mentioned above, especially when using water as a solvent, it is necessary to control the vaporizing rate to 40 kg/m²·hr or less, preferably 20 kg/m²·hr or less, or to use an aqueous mixed solvent containing a lower alcohol, preferably a $C_{1-6}$ alkyl alcohol at a vaporizing rate of 400 kg/m²·hr or less, preferably 200 kg/m²·hr or less. Methanol and ethanol are preferably used as the lower alcohol. Methanol is the most preferred lower alcohol since α-APM can undergo ester exchange reactions under some conditions reducing the overall yield of the process. The solid-liquid separability of the crystals deteriorates if the alcohol concentration is too high. Therefore, the alcohol concentration is preferably in the range of from 10–60% by volume of the solvent.

The concentration of α-APM in the starting solution is preferably a saturated solution in the solvent used at 30° C. or higher, e.g. the solubility of α-APM at 30° C. is 1.3 g/dl, since a dilute solution requires greater concentration to effect precipitation. The solubility of α-APM increases at higher temperatures, however, decomposition of α-APM simultaneously occurs, so, the maximum concentration of the starting solution should be the concentration at 80° C., for example. A preferred range of the α-APM concentration in the starting solution is 2–15 wt. %, more preferably 3–10 wt. %.

The present method of α-APM crystallization overcomes deposition problems during crystallization. Use of water or an aqueous solvent containing a lower alcohol in the present process substantially improves the solid-liquid separability of α-APM crystals and also noticeably improves the yield of crystals. The present method has practical utility due to its simplicity and use with conventional equipment.

Other features of the invention will become apparent in the course of the following descriptions of exemplary embodiments which are given for illustration of the invention and are not intended to be limiting thereof.

EXAMPLES

The test for evaluating the filterability of α-APM crystals obtained in the Examples is described below.

Method of Measuring Filtration Specific Cake Resistance

One liter of a sample to be tested was sampled and filtered through a top-feed suction filter system (leaf tester). The pressure difference during filtration was 70 mm Hg, which was kept constant throughout the period of filtration. From the start of filtration, the amount of the filtrate V(ml) was measured at regular intervals and plotted on a graph having the amount of the filtrate as the horizontal axis and the value $\theta/V$, obtained by dividing the time of filtration $\theta$ (see) by the amount of the filtrate, as the vertical axis. The slope of the line K(sec/ml²) was obtained by the least squares method. The value C', obtained by dividing the total amount (g) of the crystals in the slurry by the total amount (cm³) of the liquid in the slurry, was used in the following equation, where filtration area A is 93 (cm³) and the viscosity $\mu$ of the filtrate is 0.0135 (g/cm.sec). The specific cake resistance $\alpha$ (m/kg) thus calculated is a measure of the filterability of the sample. Samples having a lower value $\alpha$ are more easily filtered.

Equation for specific cake Resistance $\alpha = 20.K.A^2.PT/\mu.C'$ (m/kg)

where $\alpha$ is the specific cake resistance (m/kg) of the filtered cake;

$\mu$ is the viscosity of the filtrate (g/cm.sec);

PT is the pressure difference (dyne/cm²) of the filtered cake and the filtration device = $\Delta$ P(mm Hg) × 1333.22;

A is the filtration area (cm²); and

C' is the weight of the crystals per unit volume of the liquid component in the slurry (g/ml) = dry cake weight (g)/(wet cake weight (g) − dry cake weight (g) + amount of final filtrate (ml)).

EXAMPLE 1

A pilot plant system having the configuration shown in FIG. 1 was used. An aqueous α-APM solution having an α-APM concentration of 4.5 wt. % and a liquid temperature of 65° C. was fed into the 200-liter jacketed crystallizer (1), the inner pressure in the crystallizer was kept at from 8 to 10 Torr by an external pressure-reducing device (2), and the liquid temperature in the crystallizer was kept at 10° C. by the latent heat of vaporization without cooling or heating. The vaporizing rate of the water solvent was 40 kg/m²·hr, and the slurry was discharged simultaneously so that the solution level in the tank was 50%. The operation was continued for 24 hours, whereupon no rapid foaming occurred during the operation and the slurry had good fluidity. The specific cake resistance value of the slurry obtained was $7 \times 10^{10}$ (m/kg). After being filtrated with a small centrifuge followed by dewatering for 15 minutes, the crystals had a moisture content of 65%.

EXAMPLE 2

The same experiment as that in Example 1 was repeated, except that the vaporizing rate of the water solvent was varied to 20 kg/m$^2$·hr. The operation was continued for 24 hours, whereupon no rapid bubbling or foaming occurred during the operation and the slurry had good fluidity. The specific cake resistance value of the slurry obtained was $5.0 \times 10^{10}$ m/kg. After dewatering for 15 minutes, the crystals had a moisture content of 62.1%.

COMPARATIVE EXAMPLE 1

The same operation as Example 1 was carried out except that a vaporizing rate of 100 kg/m$^2$·hr was used. Just after the start of the operation the surface of the solution rose about one meter and it became difficult to continue the operation. The operation was stopped after 5 hours.

EXAMPLE 3

The same apparatus as used in Example 1 was used. An aqueous 30% methanol solution of α-APM having an α-APM concentration of 4.3 wt. % and a liquid temperature of 50° C. was fed into the crystallizer (1) at a feed rate of 188 liters per hour (average), the inner pressure in the crystallizer was kept at about 30 Torr using the external pressure-reducing device (2), and the liquid temperature in the crystallizer was kept at 20° C. The vaporizing rate of the solvent was 53 kg/m$^2$·hr, and the slurry was discharged at a rate of 176 liters per hour (average) to keep the slurry level constant. The operation was continued for 24 hours, whereupon no rapid foaming occurred during the operation and the slurry had good fluidity. The specific cake resistance value of the slurry obtained was $8.6 \times 10^9$ m/kg. After dewatering for 15 minutes with a centrifuge, the crystals had a moisture content (loss on dry) of 44%.

EXAMPLE 4

The same apparatus as used in Example 1 was used. An aqueous 30% methanol solution of α-APM having an α-APM concentration of 3.7 wt. % and a liquid temperature of 42° C. was fed into the crystallizer (1) at a feed rate of 237 liters per hour (average), and the inner pressure in the crystallizer was kept at about 30 Torr using the external pressure-reducing device (2). A part of the α-APM solution was removed from the crystallizer and heated with an external heat exchanger (3), to keep the liquid temperature in the crystallizer at 20° C. The concentration rate was controlled to 0.8. The vaporizing rate of the solvent was 160 kg/m$^2$·hr, and the circulating speed of the solution was 0.4 m$^3$/hr. The operation was continued for 24 hours, whereupon no rapid foaming occurred during the operation and the slurry had good fluidity. The specific cake resistance value of the slurry obtained was $2.8 \times 10^9$ m/kg. After dewatering for 15 minutes with centrifuge, the crystals had a moisture content (loss on dry) of 37.5%.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method of crystallizing α-L-aspartyl-L-phenylalanine methyl ester from a water solution thereof, comprising:
    crystallizing α-L-aspartyl-L-phenylalanine methyl ester in a crystallizer, wherein the pressure in the crystallizer is maintained at not higher than atmospheric pressure to vaporize said water at a rate of 40 kg/m$^2$·hr or less, and cool said solution by the latent heat of vaporization.

2. The method of claim 1, wherein said pressure in the crystallizer is 100 Torr or less.

3. The method of claim 1, wherein said pressure in the crystallizer is 50 Torr or less.

4. The method of claim 1, wherein the temperature of said water solution is 20° C. or less during said crystallizing step.

5. The method of claim 4, further comprising heating said water solution indirectly with a heat exchange means during said crystallizing step.

6. The method of claim 1, wherein said water solution is continuously fed to the crystallizer, maintaining a substantially uniform depth of water solution in said crystallizer to form a concentrated slurry.

7. The method of claim 6, further comprising continuously discharging said concentrated slurry from said crystallizer.

8. The method of claim 1, wherein said water is vaporized at a rate of 20 kg/m$^2$·hr or less.

9. A method of crystallizing α-L-aspartyl-L-phenylalanine methyl ester from a mixed solvent solution of water and a lower alcohol thereof, comprising:
    crystallizing α-L-aspartyl-L-phenylalanine methyl ester in a crystallizer, wherein the pressure in the crystallizer is maintained at not higher than atmospheric pressure to vaporize said mixed solvent at a rate of 400 kg/m$^2$·hr or less, and cool said mixed solvent solution by the latent heat of vaporization.

10. The method of claim 9, wherein said mixed solvent solution is concentrated by vaporizing said solvent.

11. The method of claim 9, wherein said lower alcohol is methanol.

12. The method of claim 11, wherein the methanol concentration in said solution is from 10 to 60% by volume.

13. The method of claim 9, wherein said pressure in the crystallizer is 100 Torr or less.

14. The method of claim 9, wherein said pressure in the crystallizer is 50 Torr or less.

15. The method of claim 9, wherein the temperature of said mixed solvent solution is 20° C. or less during said crystallizing step.

16. The method of claim 15, further comprising heating said mixed solvent solution indirectly with a heat exchange means during said crystallizing step.

17. The method of claim 9, wherein said mixed solvent solution is continuously fed to the crystallizer, maintaining a substantially uniform depth of mixed solvent solution in said crystallizer to form a concentrated slurry.

18. The method of claim 17, further comprising continuously discharging said concentrated slurry from said crystallizer.

19. The method of claim 9, wherein said mixed solvent is vaporized at a rate of 200 kg/m$^2$·hr or less.

* * * * *